United States Patent
Wagner

(10) Patent No.: US 11,490,639 B2
(45) Date of Patent: Nov. 8, 2022

(54) DENTAL COMPOSITION AND METHOD

(71) Applicant: Solarvest BioEnergy Inc., Montague (CA)

(72) Inventor: Richard E. Wagner, Bloomington, IN (US)

(73) Assignee: Solarvest BioEnergy Inc., Montague (CA)

( * ) Notice: Subject to any disclaimer, the term of this patent is extended or adjusted under 35 U.S.C. 154(b) by 0 days.

(21) Appl. No.: 15/269,176

(22) Filed: Sep. 19, 2016

(65) Prior Publication Data
US 2017/0007536 A1    Jan. 12, 2017

Related U.S. Application Data

(63) Continuation of application No. 12/692,081, filed on Jan. 22, 2010, now abandoned.

(60) Provisional application No. 61/205,633, filed on Jan. 22, 2009.

(30) Foreign Application Priority Data

Jan. 22, 2009    (EP) ..................................... 09151157
Jul. 21, 2009    (CA) ..................................... 2673636

(51) Int. Cl.
| A23K 10/30 | (2016.01) |
| A61Q 11/00 | (2006.01) |
| A23K 50/42 | (2016.01) |
| A61K 8/9722 | (2017.01) |

(52) U.S. Cl.
CPC .............. *A23K 10/30* (2016.05); *A23K 50/42* (2016.05); *A61K 8/9722* (2017.08); *A61Q 11/00* (2013.01)

(58) Field of Classification Search
CPC ...... C12N 15/82; C12N 1/12; C12N 2500/72; C12N 5/0606; C12N 1/125; A61K 8/9722; A61K 36/05; A61K 8/9706; A61Q 11/00; A23L 13/424; A23L 17/60; A23L 2/52; A23K 10/30; A23K 50/42
See application file for complete search history.

(56) References Cited

U.S. PATENT DOCUMENTS

| 3,535,421 | A | 10/1970 | Briner et al. |
| 3,678,154 | A | 7/1972 | Widder |
| 4,776,853 | A | 10/1988 | Klement et al. |
| 4,902,508 | A | 2/1990 | Badylak et al. |
| 4,992,207 | A | 2/1991 | Darnell et al. |
| 5,281,422 | A | 1/1994 | Badylak et al. |
| 5,372,821 | A | 12/1994 | Badylak et al. |
| 5,484,719 | A | 1/1996 | Lam et al. |
| 5,573,784 | A | 11/1996 | Badylak et al. |
| 5,654,184 | A | 8/1997 | Curtiss, III et al. |
| 5,661,017 | A | 8/1997 | Dunahay et al. |
| 5,670,191 | A | 9/1997 | Cummings et al. |
| 5,670,349 | A | 9/1997 | Cramer et al. |
| 5,679,880 | A | 10/1997 | Curtiss, III et al. |
| 5,686,079 | A | 11/1997 | Curtiss, III et al. |
| 5,686,125 | A | 11/1997 | Mueller |
| 5,744,515 | A | 4/1998 | Clapper |
| 5,804,408 | A | 9/1998 | Hagiwara et al. |
| 5,821,087 | A | 10/1998 | Lowe et al. |
| 5,914,123 | A | 6/1999 | Arntzen et al. |
| 5,958,422 | A | 9/1999 | Lomonossoff |
| 6,034,298 | A | 3/2000 | Lam et al. |
| 6,136,320 | A | 10/2000 | Arntzen et al. |
| 6,265,438 | B1 | 7/2001 | Steward |
| 6,270,347 | B1 | 8/2001 | Webster et al. |
| 6,444,805 | B1 | 9/2002 | Sohn et al. |
| 6,805,898 | B1 | 10/2004 | Wu et al. |
| 6,932,980 | B1* | 8/2005 | Sayre .................. A23K 20/147 424/195.17 |
| 7,393,999 | B1 | 7/2008 | Navarro Acevedo et al. |
| 7,465,784 | B2 | 12/2008 | Wang |
| 2002/0167118 | A1 | 11/2002 | Billiet et al. |
| 2002/0173033 | A1 | 11/2002 | Hammerick et al. |
| 2002/0173213 | A1 | 11/2002 | Chu et al. |
| 2003/0040809 | A1 | 2/2003 | Goldmann et al. |
| 2003/0050711 | A1 | 3/2003 | Laurencin et al. |
| 2003/0232021 | A1* | 12/2003 | Schechter ................ C12Q 1/18 424/49 |
| 2004/0028875 | A1 | 2/2004 | Van Rijn et al. |
| 2004/0104672 | A1 | 6/2004 | Shiang et al. |

FOREIGN PATENT DOCUMENTS

| EP | 0108580 A | 5/1984 |
| EP | 0342824 A | 11/1989 |
| EP | 0773295 | 5/1997 |
| EP | 0971034 A | 1/2000 |
| EP | 1114867 A | 7/2001 |
| EP | 1437124 B1 | 7/2004 |

(Continued)

OTHER PUBLICATIONS

Vanderveen et al., Nutritional Value of Algae Grown Under Sterile Conditions, Biologistics for Space Systems Symposium, Wright-Patterson Air Force Base, Dayton, Ohio, 1962, pp. 357-364.*
Se-Kwon Kim, Handbook of Marine Macroalgae, Wiley-Blackwell, pp. 1-6, 2012.*
CDA Journal Halitosis webpage (1997).
Critical Reviews in Oral Biology and Medicine (2004).
Dealtime webpage Jason Cosmetics (downloaded on Feb. 10, 2006) 3 pages.
International Dental webpage PlaqueOff (downloaded on Feb. 10, 2006) 4 pages.
News Release Jul. 21, 2008, 2 pages.
News Release Jul. 22, 2008, 2 pages.
News Release Jul. 24, 2008, 1 page.
Plant pathogen interaction Rajamani abstract (2005).

(Continued)

*Primary Examiner* — Lezah Roberts
(74) *Attorney, Agent, or Firm* — Dunlap Codding, P.C.

(57) ABSTRACT

Dental compositions that comprise algae are disclosed. Methods of use of the dental compositions, including methods of reducing plaque on at least one tooth of an animal using the dental compositions, are also disclosed.

17 Claims, 3 Drawing Sheets

(56) References Cited

FOREIGN PATENT DOCUMENTS

| EP | 1328285 | | 3/2006 |
|---|---|---|---|
| JP | 409048715 | * | 2/1997 |
| JP | 2001240604 | | 9/2001 |
| WO | 199611707 A | | 4/1996 |
| WO | 199739106 A | | 10/1997 |
| WO | 199944573 | | 9/1999 |
| WO | 199960838 A | | 12/1999 |
| WO | 200073455 | | 12/2000 |
| WO | 200198335 | | 12/2001 |
| WO | WO 2007/079120 | * | 7/2007 |
| WO | 2008021223 | | 2/2008 |

OTHER PUBLICATIONS

PlaqueOff Article (Dec. 17, 2007).
Vitamin Shoppe webpage Jason Cosmetics (downloaded on Feb. 10, 2006) 2 pages.
Wikner et al.; KI studie (available at http://www.biodistra.se/images/KI%20studie.pdf on Jul. 31, 2008, 8 pages.
U.S. Appl. No. 12/692,081; Richard E. Wagner, filed Jan. 22, 2010; Office Action dated Mar. 19, 2012.
U.S. Appl. No. 12/692,081; Richard E. Wagner, filed Jan. 22, 2010; Response to Office Action dated Sep. 19, 2012.
U.S. Appl. No. 12/692,081; Richard E. Wagner, filed Jan. 22, 2010; Office Action dated Oct. 10, 2012.
U.S. Appl. No. 12/692,081; Richard E. Wagner, filed Jan. 22, 2010; Response to Office Action dated Apr. 10, 2013.
U.S. Appl. No. 12/692,081; Richard E. Wagner, filed Jan. 22, 2010; Final Office Action dated Aug. 2, 2013.
U.S. Appl. No. 12/692,081; Richard E. Wagner, filed Jan. 22, 2010; Response to Final Office Action and Request for Continued Examination dated Feb. 3, 2014.
U.S. Appl. No. 12/692,081; Richard E. Wagner, filed Jan. 22, 2010; Office Action dated Oct. 27, 2014.
U.S. Appl. No. 12/692,081; Richard E. Wagner, filed Jan. 22, 2010; Response to Office Action dated Apr. 27, 2015.
U.S. Appl. No. 12/692,081; Richard E. Wagner, filed Jan. 22, 2010; Final Office Action dated Aug. 18, 2015.
U.S. Appl. No. 12/692,081; Richard E. Wagner, filed Jan. 22, 2010; Notice of Appeal dated Feb. 18, 2016.
Alabi, et al.; "The Efficacy of Immersion as Opposed to Oral Vaccination of Penaeus indicus Larvae Against Vibrio harveyi," Aguaculture (1999), vol. 178, pp. 1-11.
Arnon, Daniel I.; "Copper Enzymers in Isolated Chloroplasts. Polyphenoloxidase in Beta Vulgaris," Plant Physiology (1949), vol. 24, No. 1, pp. 1-15.
Blowers, A. et al.; "Studies on Chlamydomonas Chloroplast Transformation: Foreign DNA Can Be Stably Maintained in the Chromosome," The Plant Cell (1989), vol. 1, pp. 123-132.
Blowers, A. et al.; "Transcriptional Analysis of Endogenous and Foreign Genes in Chloroplast Transformants of Chlamydomonas," The Plant Cell (1990), vol. 2, pp. 1059-1070.
Brown, et al.; "Introduction of exogenous DNA into Chlamydomonas Reinhardtii by Electroporation," Molecular and Cellular Biology (1991), vol. 11, No. 4, pp. 2328-2332.
Brown S.; "Metal-Recognition by Repeating Polypeptides," Nature Biotechnology (1997), vol. 15, pp. 269-272.
Burow, et al; "Isolation of cDNA Clones of Genes Induced Upon Transfer of Chlamydomonas Reinhardtii Cells to Low C02," Plant Molecular Biology (1996), vol. 31, No. 2, pp. 443-448.
Cai, X, et al.; "Applications of Eukaryotic Algae for the Removal of Heavy Metals from Water," Molecular Marine Biology and Biotechnology (1995), vol. 4, pp. 338-344.
Cai, X, et al.; "Growth and Heavy Metal Binding Properties of Transgenic Chlamydomonas Expressing a Foreign Metallothionein Gene," Int. J. Phytoremediation (1999), vol. 1, pp. 53-65.
Cai, X, et al.; "Heavy Metal Binding Properties of Wild Type and Transgenic Algae (*Chlamydomonas* sp.)," New Developments in Marine Biotechnology (1998), pp. 189-192.
Chaney, et al.; "Phytoremediation of Soil Metals," Curr. Opin. Biotech. (1997), vol. 8, pp. 279-284.
Chen Z., et al.; "Cloning and Overexpression of Two cDNAs Encoding the Low-CO2-Inducible Chloroplast Envelope Protein LIP-36 from Chlamydomonas Reinhardtii," Plant Physiol. (1997), vol. 114, pp. 265-273.
Davies, et al.; "Expression of the Arylsulfatase Gene from the β2-tubulin Promoter in Chlamydomonas Reinhardtii," Nucleic Acids Research (1992), vol. 20, No. 12, pp. 2959-2965.
Debuchy et al.; "The Argininosuccinate Lyase Gene of Chlamydomonas Reingardtii; an Important Tool for Neclear Transformation and for Correlating the Genetic and Molecular Maps of the ARG7 Locus," EMBO Journal (1989), vol. 8, pp. 2803-2809.
D'Souza, et al.; "Effects of Monospecific and Mixed-Algae Diets on Survival, Development and Fatty Acid Composition of Penaeid Prawn (*Penaeus* spp.) Larvae," Marine Biology (1999), vol. 133, pp. 621-633.
Eibl, C., et al.; "In Vivo Analysis of Plastid psbA rbcL and rpl32 UTR Elecemts by Chloroplast Transformation: Tobacco 4 Plastid Gene Expression is Controlled by Modulation of Transcript Levels and Translation Efficiency," The Plant Journal (1999), vol. 19, No. 3, pp. 333-345.
Gorman, et al.; "Cytochrome F and Plastocyanin: Their Sequence in the Photosynthetic Electron Transport Chain of Chlamydomonas Reinhardi," P.N.A.S. (1965), vol. 54, pp. 1665-1669.
Gudding, et al.; "Recent Developments in Fish Vaccinology," Vertinary Immunology and Immunopathology (1999), vol. 72, pp. 203-212.
Haq, et al.; "Oral Immunization with a Recombinant Bacterial Antigen Produced in Transgenic Plants," Science (1995), vol. 268, pp. 714-716.
Harford, C. et al.; "Amino Terminal Cu(II)- and Ni(II)-Binding (ACTCUN) Motif of Proteins and Peptides: Metal Binding, DNA Cleavage, and Other Properties," Acc. Chem. Res. (1997), vol. 30, pp. 123-130.
Hilleman, M.R.; "Current Overview of the Pathogenisis and Prophylaxis of Measles with Focus on Practical Implications," Vaccine (2002), vol. 20, pp. 651-665.
Hutchison, et al.; "Chloroplast Transformation," Molecular Genetics of Photosynthesis (1996), Chapter 9, pp. 181-196.
Ishikura, et al.; "Expression of a foreign gene in Chlamydomonas Reinhardtii Chloroplast," J Biosci Bioeng. (1999), vol. 87, No. 3, pp. 307-314.
Kagi, et al.; "Biochemistry of Metallothionein," Biochemistry (1988), vol. 27, No. 23, pp. 8509-8515.
Kotrba, P. et al.; "Enhanced Bioaccumulation of Heavy Metal Ions by Bacterial Cells Due to Surface Display of Short Metal Binding Peptides," Applied and Environmental Microbiology (1999), vol. 65, pp. 1092-1098.
Mason, et al.; "Transgenic Plants as Vaccine Production Systems," Tibtech (1995), vol. 13, pp. 388-392.
Misra, et al.; "Heavy Metal Tolerant Transgenic *Brassica napus* L. and *Nicotiana tabacum* L. Plants," Theor. Appl. Genet. (1989), vol. 78, pp. 161-168.
Moffat; "Exploring Transgenic Plants as a New Vaccine Source," Science (1995), vol. 268.
Nucifora, G., et al.; "Cadmium Resistance from *Staphylococcus ureus* Plasmid pl258 cadA Gene Results from a Cadmium-Efflux ATPase," Proc. Nat. Acad. Sci. (1989), vol. 86, pp. 3544-3548.
O'Farrell, et al.; "Defferential Expression of the Virulence-Associated Protein P57 and Characterization of its Duplicated Gene MSA in Virulent and Attenuated Strains of Renibecterium Salmoninarum," Diseases of Aquatic Organisms (1999), vol. 38, No. 2, pp. 115-123.
Patwardhan A., et al.; "Phage-Displayed Libraries for the Selection of Optimal Affinity Peptides for Protein Purification Using Ni-Nitrilotriacetic Acid Chromatography," Biotech. Techniq. (1998), vol. 12, pp. 421-424.
Patwardhan A., et al.; "Selection of Optimum Affinity Tags from a Phage-Displayed Peptide Library: Application to Immobilized Copper(II) Affinity Chromatography," J. Chromat. (1997), vol. 787, pp. 91-100.

(56) References Cited

OTHER PUBLICATIONS

Piganelli, et al.; "Evaluation of a Whole Cell, p57—Vaccine Against Renibacterium Salmoninarum," Diseases of Aquatic Organisms (1999), vol. 36, No. 1, pp. 37-44.

Regan, L.; "Protein Design: Novel Metal-Binding Sites," TIBS (1995), vol. 20, pp. 280-285.

Ruffle, et al.; "Functional Analysis of Photosystem II," The Molecular Biology of Cholorplasts and Mitochondria in Chlamydomonas, (1998), Chapter 16, pp. 287-322.

Scapigliati, G., et al.; "The Immune System of Sea Bass, *Dicentrarchus labrax*, Reared in Aquaculture," Dev Comp Immuno (2002), vol. 26, pp. 151-160.

Silver, S.; "Bacterial Resistance ATPases: Primary Pumps for Exporting Toxic Cations and Anions, Trends," Biol. Sci. (1989), vol. 14, pp. 76-80.

Shimogawara, et al.; "High-Efficiency Transformation of Chlamydomonas Reinhardtii by Electroporation," Genetics (1998), vol. 148, pp. 1821-1828.

Siripornadulsil , S., et al.; "Psscr7 A Transformation Vector for Expression of Foreign Genes in the Nuclear Genome of Chlamydomonas Reinhardtii," presented at the Northeast Algal Society Meeting, Apr. 17, 1999.

Sousa, C., et al.; "Metalloadsorption by *Escherichia coli* Cells Displaying Yeast and Mammalian Metallothioneins Anchored to the Outer Membrane Protein LamB," J. Bact. (1998), vol. 180, pp. 2280-2284.

Tohoyama H., et al.; "Resistance to Cadmium is Under the Control of the CAD2 Gene in the Yeast *Saccharomyces cerevisiae*," (1990), vol. 18, pp. 181-185.

Tsai, et al.; "Growth Enhancement of Juvenile Striped Mullet by Feeding Recombinant Yeasts Containing Fish Growth Hormone," The Progressive Fish Culturist (1994), vol. 56, pp. 7-12.

Van Muiswinkel, V.B., et al.; "The Influence of Environmental and Genetic Factors on the Disease Resistance of Fish," Aquaculture (1999), vol. 172, pp. 103-110.

Waffenschmidt, S., et al.; "Isodityrosine Cross-Linking Mediates Insolubilation of Cell Walls in Chlamydomonas," Plant Cell (1993), vol. 5, pp. 809-820.

Wiens, et al.; "Antigenic and Functional Characterization of p57 Produced by Renibacterium Salmoninarum," Diseases of Aquatic Organisms (1999), vol. 37, No. 1, pp. 43-52.

Wong, M.H., et al.; "Sludge-Grown Algae for Culturing Aquatic Organisms: Part II, Sludge-Grown Algae as Feeds for Aquatic Organisms," Envir. Manag. (1996), vol. 20, No. 3, pp. 375-389.

Yoon, K., et al.; "Regulation of the cadA Cadmium Resistance Deteriminant of *Staphylococcus aureus* Plasmid pI258," J. Bacteriol. (1991), vol. 173, pp. 7636-7649.

Bayer Healthcare Pressclub article (Feb. 28, 2005).

California Vet Supply webpage 2 PlaqueOff (downloaded on 047/24/2008), 3 pages.

California Vet Supply webpage PlaqueOff (downloaded on Feb. 10, 2006) 3 pages.

Hein, et al.; "Size-dependent Nitrogen Uptake in Micro- and Macroalgae," Marine Ecology Progress Series (1995) 118:247-253.

\* cited by examiner

CC-1284

CC-1952

DENTAL COMPOSITION AND METHOD

CROSS REFERENCE TO RELATED APPLICATIONS/INCORPORATION BY REFERENCE STATEMENT

This application is a continuation of U.S. Ser. No. 12/692,081, filed Jan. 22, 2010; which claims priority under 35 U.S.C. § 119(e) to U.S. Provisional Application No. 61/205,633, filed Jan. 22, 2009. The '081 application also claims the benefit of priority to European Patent Application No. 09151157.6, filed Jan. 22, 2009; and Canadian Patent Application No. 2,673,636, filed Jul. 21, 2009. The entire contents of each of the above-referenced patents and patent applications are hereby expressly incorporated by reference.

TECHNICAL FIELD

The presently disclosed and/or claimed inventive concept(s) relates to a dental composition and methods of use of the dental composition. More particularly, the presently disclosed and/or claimed inventive concept(s) relates to a dental composition for an animal wherein the composition comprises algae. The presently disclosed and/or claimed inventive concept(s) also relates to methods of use of the dental composition comprising algae, including methods of reducing plaque on at least one tooth of an animal.

BACKGROUND

Biofilm, dental plaque, and calculus, etc. are associated with bad breath and with major dental diseases, such as dental caries, gingivitis, periodontitis, and other periodontal diseases, that affect a large percentage of animals each year. Microorganisms, such as bacteria, can contribute to formation of biofilm, plaque, and calculus. Some of the types of microorganisms that are primary, secondary, or tertiary colonizers of biofilm (e.g. dental plaque, calculus, etc.) are *Streptococcus mutans, Streptococcus sanguis, Actinomyces viscosus, Lactobacillus acidophilus, Actinobacillus actinomycetemcomitans, Eikenella corrodens, Porphyromonas gingivalis, Prevotella intermedia, Bacteroides forsythus, Campylobacter rectus, Treponema denticola, Fusobacterium nucleatum, Capnocytophypa* species, *Tannerella* species, *Peptostreptococcus* species, *Endodontalis* species, and *Escherichia* species.

The formation of biofilm, plaque, and calculus is not only associated with a variety of dental diseases, including dental caries, tooth loss, and periodontitis, but can lead to poor health generally in animals by contributing to the development of systemic diseases of major organ systems such as kidney disease, vascular diseases, and heart disease. Accordingly, there is a need for effective methods of reduction of biofilm, plaque, and calculus on the teeth of animals to improve animal dental health, and to improve animal health generally.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
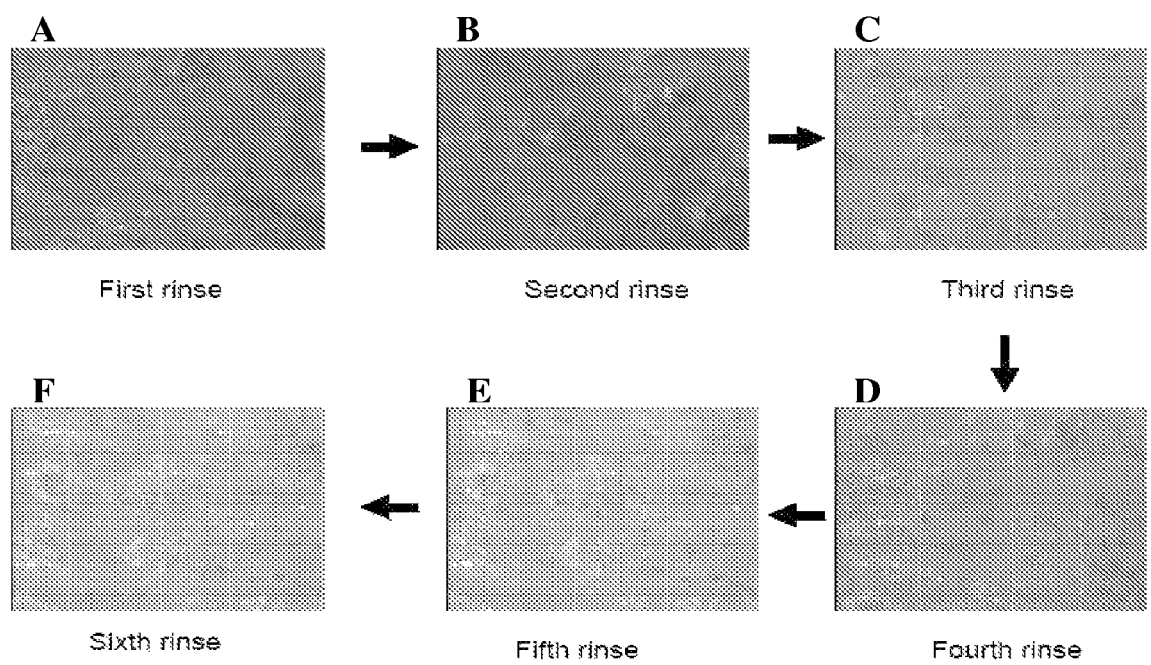
FIG. 1 shows cells of CC-1284 remaining on a molar following coating the molar with an algal paste and successive rinses with deionized water. Panels A-F represent the first through sixth rinses, respectively.

While the presently disclosed and/or claimed inventive concept(s) is susceptible to various modifications and alternative forms, illustrative embodiments are described herein. It should be understood, however, that there is no intent to limit the presently disclosed and/or claimed inventive concept(s) to the particular forms described, but on the contrary, all modifications, equivalents, and alternatives falling within the spirit and scope of the presently disclosed and/or claimed inventive concept(s) are covered.

The presently disclosed and/or claimed inventive concept(s) is directed to the surprising discovery that compositions comprising algae (e.g., green algae) reduce plaque on the teeth of animals. In fact, plaque reduction can occur, for example, by early times (e.g., about 24 hours) after administration of the algae composition. Algae compositions are desirable for use in such dental compositions because algae are natural, non-toxic, non-pathogenic, free of animal pathogens, easy to grow, and resistant to degradation by acids present in the mouth.

In one embodiment of the presently disclosed and/or claimed inventive concept(s), a method is provided for reducing plaque on at least one tooth of an animal. The method comprises the step of causing the at least one tooth of the animal to be contacted with a composition comprising green algae wherein the composition comprising the green algae reduces the plaque on the at least one tooth of the animal. In this embodiment, the algae can be in the form of a paste, a gel, a liquid (e.g., for addition to the drinking water of the animal), a powder, a freeze-dried composition, a component of an animal treat, a nugget, a dressing for an animal food, an additive for water, a component of a chew product, or a pellet. In any of these embodiments directed to the form of the algae, the algae can be freeze-dried prior to formulating any of these compositions, and can be thawed and reconstituted to formulate the composition. Alternatively, the algae can be present in the composition in a freeze-dried form.

In illustrative aspects of any of the above-described method embodiments, the algae can be genetically modified (e.g., to express an antimicrobial peptide). In yet other illustrative embodiments of the above-described method embodiments, the algae composition can further comprise one or more of a preservative, an inert carrier (e.g., selected from the group consisting of a paste and a gel), a flavoring, a nutritional carrier, a nutraceutical, a material to enhance adhesion of the algae to at least one tooth of an animal, an antimicrobial (e.g., an antimicrobial peptide or an antibiotic), a plaque-reducing agent, and a calculus-reducing agent.

In still other illustrative embodiments of any of the above-described method embodiments, the algae can be selected from the group consisting of live algae, dead algae, and combinations thereof, or the algae can be of the species *Chlamydomonas reinhardtii*. In any of the above-described method embodiments, the animal treated with the algae composition can be, for example, a cat or a dog. In any of the above-described method embodiments, the algae can adhere to the at least one tooth for a prolonged period of time and the plaque can be present on more than one tooth.

In another embodiment of the presently disclosed and/or claimed inventive concept(s), a composition comprising green algae is provided, wherein the green algae composition is adapted for contact with at least one tooth of an animal. In this composition embodiment, the algae can be in the form of a paste, a gel, a liquid (e.g., for addition to the drinking water of the animal), a powder, a freeze-dried composition, a component of an animal treat, a nugget, a dressing for an animal food, an additive for water, a component of a chew product, or a pellet. In another illustrative embodiment, the algae can be freeze-dried and can be capable of being reconstituted.

In another illustrative aspect of the above-described algae composition embodiment, the algae can be genetically modified (e.g., to express an antimicrobial peptide).

In yet another embodiment, the algae composition can further comprise one or more of a preservative, an inert carrier (e.g., selected from the group consisting of a paste and a gel), a flavoring, a nutritional carrier, a nutraceutical, a material to enhance adhesion of the algae to at least one tooth of an animal, an antimicrobial (e.g., an antimicrobial peptide or an antibiotic), a plaque-reducing agent, and a calculus-reducing agent.

In still other illustrative embodiments, the algae can be selected from the group consisting of live algae, dead algae, and combinations thereof, or the algae can be of the species *Chlamydomonas reinhardtii*.

In yet another method embodiment, a method is provided for reducing plaque on at least one tooth of an animal. The method comprises the step of causing the at least one tooth of the animal to be contacted with a composition comprising algae wherein the composition comprising the algae reduces the plaque on the at least one tooth of the animal and wherein the composition comprising the algae acts directly on the at least one tooth.

In the method embodiment described in the preceding paragraph, the algae can be selected from the group consisting of green algae, brown algae, red algae, and diatoms. In additional embodiments the algae can be in the form of a paste, a gel, a liquid (e.g., for addition to the drinking water of the animal), a freeze-dried composition, a powder, a component of an animal treat, a nugget, a dressing for an animal food, an additive for water, a component of a chew product, or a pellet. In another illustrative embodiment, the algae can be freeze-dried and can be capable of being reconstituted.

In illustrative aspects of this method embodiment, the algae can be genetically modified (e.g., to express an antimicrobial peptide). In yet another embodiment of this method, the algae composition can further comprise one or more of a preservative, an inert carrier (e.g., selected from the group consisting of a paste and a gel), a flavoring, a nutritional carrier, a nutraceutical, a material to enhance adhesion of the algae to at least one tooth of an animal, an antimicrobial (e.g., an antimicrobial peptide or an antibiotic), a plaque-reducing agent, and a calculus-reducing agent.

In still other illustrative embodiments of the above-described method embodiment, the algae can be selected from the group consisting of live algae, dead algae, and combinations thereof, or the algae can be of the species *Chlamydomonas reinhardtii*. In other embodiments, the animal treated with the algae composition can be, for example, a cat or a dog. In another illustrative aspect, the algae can adhere to the at least one tooth for a prolonged period of time and the plaque can be present on more than one tooth.

In yet another illustrative aspect, a kit is provided. The kit comprises a green algae composition wherein the green algae composition is adapted for contact with at least one tooth of an animal. In this embodiment, the kit further comprises an applicator for rubbing the green algae composition on the at least one tooth of the animal. In another embodiment, the kit comprises a syringe for applying the algae composition to the teeth. In any of these embodiments, the kit can comprise instructions for use.

In this kit embodiment, the algae can be in the form of a paste, a gel, a liquid (e.g., for addition to the drinking water of the animal), a powder, a freeze-dried composition, or an additive for water. In another illustrative kit embodiment, the algae can be freeze-dried and can be capable of being reconstituted.

In illustrative aspects of the above-described kit embodiment, the algae can be genetically modified (e.g., to express an antimicrobial peptide). In yet another kit embodiment, the algae composition can further comprise one or more of a preservative, an inert carrier (e.g., selected from the group consisting of a paste and a gel), a flavoring, a nutritional carrier, a nutraceutical, a material to enhance adhesion of the algae to at least one tooth of an animal, an antimicrobial (e.g., an antimicrobial peptide or an antibiotic), a plaque-reducing agent, and a calculus-reducing agent.

In still other illustrative kit embodiments, the algae can be selected from the group consisting of live algae, dead algae, and combinations thereof, or the algae can be of the species *Chlamydomonas reinhardtii*. In another illustrative kit embodiment, the algae can adhere to the at least one tooth for a prolonged period of time and the algae composition can cause plaque reduction on at least one tooth of an animal.

In yet another embodiment, an article of manufacture is provided. The article of manufacture comprises a commercial package containing a composition comprising green algae adapted for contact with at least one tooth of an animal. In this embodiment, the article of manufacture can be air-tight and can also be leak-resistant.

In this article of manufacture embodiment, the algae can be in the form of a paste, a gel, a liquid (e.g., for addition to the drinking water of the animal), a powder, a freeze-dried composition, a component of an animal treat, a nugget, a dressing for an animal food, an additive for water, a component of a chew product, or a pellet. In another illustrative embodiment, the algae can be freeze-dried and can be capable of being reconstituted.

In illustrative aspects of the above-described article of manufacture embodiment, the algae can be genetically modified (e.g., to express an antimicrobial peptide). In yet another article of manufacture embodiment, the algae composition can further comprise one or more of a preservative, an inert carrier (e.g., selected from the group consisting of a paste and a gel), a flavoring, a nutritional carrier, a nutraceutical, a material to enhance adhesion of the algae to at least one tooth of an animal, an antimicrobial (e.g., an antimicrobial peptide or an antibiotic), a plaque-reducing agent, and a calculus-reducing agent.

In still other illustrative article of manufacture embodiments (referred to herein as embodiments A), the algae can be selected from the group consisting of live algae, dead algae, and combinations thereof, or the algae can be of the species *Chlamydomonas reinhardtii*. In other article of manufacture embodiments, the animal treated with the algae composition can be, for example, a cat or a dog. In another illustrative aspect, the algae can adhere to the at least one tooth for a prolonged period of time and the algae composition can cause plaque reduction.

For all of the above-described embodiments, any applicable combination of embodiments is also contemplated (e.g., an algae composition could further comprise an inert carrier, a flavoring, and a nutritional carrier or the algae could be genetically modified and the algae composition could further comprise an inert carrier, a flavoring, and a nutritional carrier). Any applicable combination of the above-described embodiments (referred to herein as embodiments B) is considered to be in accordance with the presently disclosed and/or claimed inventive concept(s).

In another embodiment (referred to herein as embodiment C), a composition comprising algae for reducing plaque on at least one tooth of an animal is provided.

In yet another embodiment, a composition comprising algae is provided wherein the algae composition is adapted for contact with at least one tooth of an animal. In this embodiment, 1) the algae composition can be selected from green algae, red algae, and diatoms, 2) the algae can be green algae, 3) the algae can be in the form of a paste, gel, liquid, nugget, powder, pellet, dressing for animal food or an additive for drinking water or are a component of an oral or digestible treat or chew product, 4) the algae can be freeze-dried and are capable of being reconstituted, 5) the algae can be genetically modified, 6) the algae can be genetically modified to express an antimicrobial peptide, 7) the algae composition can further comprises a preservative, flavoring, inert carrier or nutritional carrier, 8) the inert carrier can be selected from a paste and a gel, 9) the algae composition can further comprise a material to provide adhesion of the algae to the at least one tooth, 10) the algae composition can further comprise an antimicrobial peptide or other antimicrobial, an antibiotic, an additional plaque-reducing agent or a calculus-reducing agent, 11) the algae can be selected from live algae, dead algae, and combinations thereof, 12) the algae can be from the species *Chlamydomonas reinhardtii*, 13) the animal can be a dog or a cat, or 14) the algae can adhere to the at least one tooth for a prolonged period of time. Any combination of embodiments A above with 1-14, or any combination thereof, is contemplated.

In still another embodiment, a kit is provided comprising an algae composition wherein the algae composition is adapted for contact with at least one tooth of an animal. In this embodiment, 1) the algae can be green algae, 2) the kit can further comprise an applicator for rubbing the green algae composition on the at least one tooth of the animal, or 3) the kit can further comprise a syringe. Any combination of embodiments B above with 1-3, or any combination thereof, is contemplated.

In a further embodiment, the use of a composition comprising algae in the manufacture of a medicament adapted for contact with at least one tooth of an animal is provided. In this embodiment, 1) the algae composition can be selected from green algae, red algae, and diatoms, 2) the algae can be green algae, 3) the algae or medicament can be in the form of a paste, gel, liquid, nugget, powder, pellet, dressing for animal food or an additive for drinking water or are a component of an oral or digestible treat or chew product, 4) the algae can be freeze-dried and are capable of being reconstituted, 5) the algae can be genetically modified, 6) the algae can be genetically modified to express an antimicrobial peptide, 7) the algae composition can further comprise a preservative, flavoring, inert carrier or nutritional carrier, 8) the inert carrier can be selected from a paste and a gel, 9) the algae composition can further comprise a material to provide adhesion of the algae to the at least one tooth, 10) the algae composition can further comprise an antimicrobial peptide or other antimicrobial, an antibiotic, an additional plaque-reducing agent or a calculus-reducing agent, 11) the algae can be selected from live algae, dead algae, and combinations thereof, 12) the algae can be from the species *Chlamydomonas reinhardtii*, 13) the animal can be a dog or a cat, or 14) the algae can adhere to the at least one tooth for a prolonged period of time. Any combination of embodiment C above with 1-14, or any combination thereof, is contemplated.

In any of the above-described embodiments, plaque reduction can occur by about 24 hours after treatment with the algae composition.

As used herein, "biofilm" means a dental biofilm.

As used herein, "calculus" means plaque that has partially or completely calcified.

As used herein, "at least one tooth" means one tooth or more than one tooth of an animal.

As used herein, "whole algae" means algae that have not been extracted (e.g., using a standard cellular extraction method known in the art).

As used herein, the terms "reducing," "reduce," "reduces," and "reduction" in reference to biofilm, plaque, or calculus mean that a lower amount of biofilm, plaque, or calculus, or a combination thereof, is found on at least one tooth of an animal after treatment with the compositions described herein, or that biofilm, plaque, or calculus, or a combination thereof, is completely removed from at least one tooth of an animal after treatment with the compositions described herein, or that biofilm, plaque, or calculus, or a combination thereof, is prevented from forming on at least one tooth of an animal after treatment with the compositions described herein.

As used herein, "green algae" means microalgae from the group Chlorophyta.

As used herein, "brown algae" means microalgae from the group Phaeophyta.

As used herein, "red algae" means microalgae from the group Rhodophyta.

As used herein, "diatoms" means microalgae from the group Bacillariophyta.

As used herein, "algae" means microalgae.

In various embodiments of the methods and compositions described herein (referred to as embodiments D), the animal treated with the algae compositions according to the methods described herein can be, for example, a domestic animal, such as a dog, a cat, or a ferret, a wild animal in captivity such as a bear, a panda, a lion, a tiger, a leopard, an elephant, a zebra, a giraffe, a monkey, a chimpanzee, or a gorilla, an equine species (e.g., a race horse), or a human. It should be understood, however, that this list of animals that can be treated using the methods and compositions described herein is non-limiting, and any type of animal in need of treatment with the methods and dental compositions described in this application can be treated.

The presently disclosed and/or claimed inventive concept(s) relates to a dental composition, kits containing the dental composition, articles of manufacture comprising the dental composition, and methods of use of the dental composition (referred to as embodiments E). More specifically, the presently disclosed and/or claimed inventive concept(s) relates to a dental composition for an animal wherein the dental composition comprises algae. The presently disclosed and/or claimed inventive concept(s) also relates to methods of use of the dental composition comprising algae, including methods of reduction of plaque on at least one tooth of an animal. The algae for use in these compositions, kits, articles of manufacture, and methods can be green algae, brown algae, red algae, or diatoms, but are typically green algae.

In one embodiment of the presently disclosed and/or claimed inventive concept(s) (referred to as embodiment F), a method is provided for reducing plaque on at least one tooth of an animal. The method comprises the step of causing the at least one tooth of the animal to be contacted with a composition comprising algae wherein the composition comprising the algae reduces the plaque on the at least one tooth of the animal and wherein the composition comprising the algae acts directly on the at least one tooth.

In another embodiment of the presently disclosed and/or claimed inventive concept(s) (referred to as embodiment G), a method is provided for reducing plaque on at least one tooth of an animal. The method comprises the step of causing the at least one tooth of the animal to be contacted with a composition comprising green algae wherein the composition comprising the green algae reduces the plaque on the at least one tooth of the animal.

In yet another embodiment of the presently disclosed and/or claimed inventive concept(s) (referred to as embodiment H), a composition comprising green algae is provided, wherein the green algae composition is adapted for contact with at least one tooth of an animal.

In another illustrative aspect of the presently disclosed and/or claimed inventive concept(s), a kit is provided. The kit comprises a green algae composition wherein the green algae composition is adapted for contact with at least one tooth of an animal. In this embodiment (referred to as embodiment I), the kit can further comprise an applicator for rubbing the green algae composition on at least one tooth of the animal. In another embodiment, the kit can comprise a syringe for application of the algae composition to at least one tooth of the animal. In yet another embodiment, the kit can contain instructions for use. Other suitable kit components include algal rinse compositions, brushes, algal paste compositions, a powdered algae composition for dispersion in the drinking water of the animal, freeze-dried algae, chew treats, and the like. The kit can also contain an algae composition that comprises green algae, brown algae, red algae, diatoms, or a combination thereof.

In yet another embodiment of the presently disclosed and/or claimed inventive concept(s), an article of manufacture is provided. The article of manufacture comprises a commercial package containing a composition comprising green algae adapted for contact with at least one tooth of an animal. In one illustrative embodiment, the article of manufacture can be packaged in an air-tight container. In another illustrative aspect, the article of manufacture can be packaged in a container that is leak-resistant.

For each of the above-described composition, kit, article of manufacture, and method embodiments, various modifications and alternative forms, and illustrative embodiments and aspects are described below. All of the illustrative embodiments, modifications, and alternative forms described below may be applied to the embodiments D-I above.

In some of the above-described embodiments, the algae are green algae. In accordance with the presently disclosed and/or claimed inventive concept(s), "green algae" means microalgae from the group Chlorophyta. In other embodiments, the algae can be any type of microalgae including, for example, green algae, brown algae, red algae, or diatoms, or combinations thereof, as long as the algae are microalgae. In accordance with the presently disclosed and/or claimed inventive concept(s), "brown algae" means microalgae from the group Phaeophyta. In accordance with the presently disclosed and/or claimed inventive concept(s), "red algae" means microalgae from the group Rhodophyta. In accordance with the presently disclosed and/or claimed inventive concept(s), "diatoms" means microalgae from the group Bacillariophyta.

In various embodiments, whole algae (e.g., whole algae, either ground algae or algae that has not been ground) can be used in the algal paste, gel, liquid, powder, freeze-dried composition, and other applicable forms that are used in accordance with the presently disclosed and/or claimed inventive concept(s). In an alternate embodiment, algae extracts, including purified components of the algae, can be used. In other illustrative embodiments, the algae can be selected from the group consisting of live algae, dead algae, and combinations thereof.

Exemplary green algae that can be used include *Chlamydomonas* species, (e.g., *Chlamydomonas reinhardtii*), *Chlorella* species, *Volvox* species, *Dunaliella* species, *Nannochloris* species, *Oedogonium* species, and some marine macrophytes.

*Chlamydomonas reinhardtii* is an exemplary green algae that can be used in the methods and compositions described herein. *Chlamydomonas reinhardtii* grows rapidly and is easy and inexpensive to grow in culture. Exemplary *Chlamydomonas* strains include CC-425, CC-741, CC-744, CC-1284, CC-1952, CC-2137, CC-2277, CC-2519 CC-2677. These strains are available from the *Chlamydomonas* Center, University of Minnesota (Minneapolis, Minn.). Exemplary website addresses include http://www.chlamy.org/chlamydb.html or http://www.chlamy.org/strains.html or http://www.chlamy.org/info.html. *Chlamydomonas* strains, or other green algae strains, are also available from the ATCC (American Type Culture Collection, P.O. Box 1549, Manassas, Va. 20108). An exemplary website address is http://www.atcc.org/ATCCAdvancedCatalogSearch/tabid/112/Default.aspx. Any suitable *Chlamydomonas* strain that can be obtained from the *Chlamydomonas* Center or the ATCC, or that is known to the skilled artisan can be used.

In illustrative embodiments, the algal cells can be cultured using a variety of techniques known in the art. Typically, algal cultures are supplemented with a carbon source (e.g., glucose or acetate), and the algal cells can be cultured to achieve a desired density. Briefly, standard sterile techniques known to those skilled in the art can be used. In one embodiment, algal cells can be inoculated into standard algal cell culture medium using a laminar flow hood to maintain sterile conditions and the algae can then be cultured with aeration at about 23° C. using 18 hour light/6 hour dark cycles. In one illustrative embodiment, progression from small cultures (e.g., 30 ml) to larger cultures (e.g., 200 ml) to large flasks (e.g., 2 liters) is used. The algal cultures are typically stirred to maintain the cells in suspension. In one embodiment, if the pH of the medium increases to above about 9, for example, the culture medium can be bubbled with $CO_2$ to reduce the pH to about 7, or an alkaline buffering compound, such as $NaHCO_3$, can be added. When a desired algal cell density is achieved, an algal cell pellet (e.g., a paste) can be collected by centrifugation, and the supernatant discarded.

In illustrative embodiments, whole algae (e.g., either algae that has been disrupted (e.g., by grinding the algae) or algae that is not disrupted) can be used in the algae paste, gel, liquid, powder, freeze-dried composition, and other applicable forms described herein. The algae can, for example, be collected from culture medium by pelleting the algae by centrifugation and the algal pellet can be used in the compositions described herein. In alternate embodiments, an algal component (e.g., a purified component) or algal components (e.g., a partially purified extract) can be used.

In embodiments where it is desirable to extract and purify a component(s) of the algae for use in the methods and compositions described herein, the algal component(s) (e.g., a protein) can be purified from the algal cell pellet after extraction of the algal cells. In one embodiment, freeze-dried algae can be extracted with a suitable solvent such as ethanol, methanol, isopropanol, or dichloromethane. In various embodiments, conventional purification techniques can be used. For purification of a component(s) from an algal cell extract, the extract can, for example, be subjected to ammonium sulfate precipitation followed by DEAE-Sepharose column chromatography. Other conventional techniques known to those skilled in the art can be used for purification such as gel filtration, ion exchange chromatography, DEAE-Sepharose column chromatography, affinity chromatography (e.g., the FLAG-tagged system described in WO 2008/021223, incorporated herein by reference), solvent-solvent extraction, ultrafiltration, tangential flow filtration, FPLC and HPLC. The purified algal component(s) can be concentrated, if desired, by such techniques as, for example, ultrafiltration and tangential flow filtration.

In one embodiment where it is desirable to extract and purify a component(s) of the algae for use in the methods and compositions described herein, the algal cells can be lysed, for example, by sonication, heat, or chemical treatment, and the lysate extracted with a suitable solvent such as ethanol, methanol, isopropanol, or dichloromethane, and then the lysate can be centrifuged to remove cell debris. The supernatant can then be subjected to fractionation techniques, as required, such as ammonium sulfate precipitation, dialysis, gel filtration, ion exchange chromatography DEAE-Sepharose column chromatography, affinity chromatography, solvent-solvent extraction, ultrafiltration, FPLC, and HPLC to purify the desired algal component(s).

In this embodiment, the algal component(s) can be purified in a substantially pure form. Exemplary substantially pure compositions can be about 40% pure, about 50% pure, about 60% pure, about 70-80% pure, about 90% pure, about 95% pure, or about 98% pure. It should be understood that the purification methods described above for purification of desired algal component(s) are nonlimiting and any purification techniques known to those skilled in the art can be used if a substantially pure algal component(s) is desired, and such techniques are required to obtain the substantially pure component(s).

For the embodiments described herein where the algae are genetically modified, exogenous nucleotides (e.g., DNA) can be introduced into the nuclear, chloroplast, or mitochondrial genome of the algae. Nuclear transformation of the algae can be performed, for example, by electroporation essentially as described in Shimogawara, et al., *Genetics* Vol. 148, 1821-1828, incorporated herein by reference. In another illustrative embodiment, nuclear, chloroplast, or mitochondrial transformation can be achieved using a transgene flanked by homologous nuclear, chloroplast, or mitochondrial targeting sequences that facilitate integration of the transgene into the desired site. See, for example, the chloroplast transformation vector described in WO 2008/021223, incorporated herein by reference. In other embodiments, other standard transformation methods known to the skilled artisan can be used including calcium phosphate precipitation, DEAF-dextran transformation techniques, and biolistics. In some embodiments, the molecule expressed (e.g., a peptide, a polypeptide, or a protein) can be expressed at high efficiency (e.g., as described in WO 2008/021223, incorporated herein by reference).

In various illustrative embodiments, the algae can be genetically modified to express a plaque-reducing agent, a calculus-reducing agent, an antimicrobial (e.g., an antimicrobial peptide), and the like. Antimicrobial peptides can include, for example, peptides that inhibit interaction or binding of microbes to components of biofilm, plaque, or calculus, peptides that interfere with the metabolism of microbes, peptides that damage the cell walls of microbes, and the like. Methods of identifying antimicrobial peptides are known in the art and are described in U.S. Pat. Nos. 7,465,784 and 7,393,999, incorporated herein by reference.

In one embodiment, auxotrophic mutants that can be used (i.e., mutants that differ from the wild-type in requiring one or more nutritional supplements for growth) are readily available at the *Chlamydomonas* Center, University of Minnesota (Minneapolis, Minn.; e.g., http://www.chlamy.org/info.html). Such mutants can be genetically complemented by transforming the mutant algae with nucleotides (e.g., exogenous DNA), which facilitates selection of transformed algae containing a desired transgene. This selection method avoids the need for the use of an antibiotic-based selection method.

In one embodiment, the genetically modified algae that express a desired protein, polypeptide, peptide, etc. are further genetically modified such that they will not proliferate in the environment in general, but rather will proliferate only in specific controlled environments (i.e., such strains will not grow or transfer their genes in the wild). In accordance with the presently disclosed and/or claimed inventive concept(s), such algae are said to be "disabled." Use of such disabled algae strains inhibits or limits spread of the genetically modified algae into the environment.

In one embodiment, disabled strains of algae can be constructed by incorporating a genetic mutation that precludes growth and/or mating outside of a specific controlled environment. For example, the genetically modified algae may be engineered to contain mutations that prevent photosynthesis, and such strains are unlikely to survive in the wild because they cannot produce the energy or reduced carbon necessary to sustain life. An exemplary mutation preventing photosynthesis is a mutation in genes comprising the psbD/psaC operon of *C. reinhardtii*, which is part of the chloroplast genome of *C. reinhardtii*. In other embodiments, mutations useful in constructing disabled algal strains are mutations in genes that result in strains that cannot grow in the absence of specific metabolites. These mutant strains are said to be "auxotrophic" for the particular metabolite (e.g, amino acids, vitamins, etc.). In various embodiments, useful mutations require cells to be grown in the presence of arginine, thiamine, or nicotinamide. In yet another embodiment, multiple mutations of the type described above, for example, are combined into a single strain of algae. Combinations of these mutations in a single strain (also called "stacking" of mutations) result in disabled strains that are particularly nonfunctional in growth and mating, and in the ability to grow and transfer their genes in the wild.

In another embodiment, a disabled algal strain takes advantage of mating events. For example, in *C. reinhardtii*, When haploid (+) and (−) cells mate to form a diploid cell, only the chloroplast genomes from the (+) mating type organism survive. The chloroplast genomes of the (−) mating type cells are degraded during mating. Accordingly, *C. reinhardtii* strains in which the transgene encoding the expressed molecule is located in the chloroplast genome of a (−) cell are advantageous when control of proliferation of transgenic algae is desired. In yet another embodiment, the algal strain can be disabled by mutations in the genes encoding flagella. For example, in *C. reinhardtii*, flagella are necessary to hold (−) and (+) cells together during mating. Accordingly, transgene-containing cells with mutations in genes encoding flagella will be unable to transmit the transgene through mating.

In various embodiments of the methods and compositions described herein, the algae can be in the form of a paste, a gel, a liquid (e.g., for addition to the drinking water of an animal), a powder, or a freeze-dried composition (e.g., a composition that is capable of being reconstituted). In one embodiment, the algae can be dried for storage and/or preservation.

In various illustrative aspects, algal pastes can be made by harvesting algal cultures by continuous centrifugation in a batch-centrifuge, where the algal pellet is collected and yields an algal paste. In an alternate embodiment, algae can be harvested by gravitational sedimentation (e.g., in a conical tank). The algal sediment can then be collected and centrifuged to yield the algal paste. In yet another embodiment, the algae may be flocculated from the culture medium by the addition of certain salts, such as ferric chloride, aluminum chloride or aluminum sulfate. The cells that settle out after flocculation may be harvested by centrifugation to generate the algal paste. In yet another embodiment, algae can be concentrated by cross-flow filtration, and then centrifuged to form an algal paste. Other methods for forming an algal paste for use in the methods and compositions described herein are known to those skilled in the art.

In another embodiment, an algal powder can be made by, for example, freeze-drying an algal paste, milling the freeze-dried algae, or grinding the algae in a Waring blender, for example, and then sieving the milled or ground algae composition to form a powder. In one embodiment, the powdered algae can be used directly in the algal compositions described herein for use in treating the teeth of animals. In another embodiment, the powdered algae can be freeze-dried for storage, and reconstituted for use in the algae compositions described herein. In another embodiment, various types of algae forms (e.g. a paste, a powder, a freeze-dried (according to protocols known in the art) algae composition, an algae composition dried in a commercial drier, etc.) can be reconstituted in, for example, a buffer solution or in water to form the liquid algae composition which is used, for example, as an additive for the drinking water of an animal. Algal gel compositions can be made according to procedures well-known to those skilled in the art.

In the above described embodiments of the algal form, the animal can be treated with the algae composition where the algae composition is a component of an animal treat, is in the form of a dressing for animal food, is in the form of a nugget, a pellet, is in the form of an additive for water, or is a component of a chew product (e.g., either an oral or digestible chew product). Any suitable regimen for treatment of the animal with the algae compositions described herein can be used. A person skilled in the art would be readily able to determine a dosing regimen depending on the type of formulation used. Exemplary treatment regimens include application of the algae composition to the teeth of the animal one or more times daily (e.g., one, two, or three times) on weekdays, and one or more times daily on weekends (e.g., one, two, or three times). In another embodiment, a daily regimen is used with application of the algae composition to the teeth of the animal once daily. Further, a staggered regimen, for example, one to three days per week can be used as an alternative to daily treatment, and for the purpose of defining the presently disclosed and/or claimed inventive concept(s) such an intermittent or staggered daily regimen is considered to be within the scope of the presently disclosed and/or claimed inventive concept(s).

In any of the embodiments described in this application the algae composition can comprise about 90% by weight of algae, about 1% to about 20% by weight of algae, about 15% to about 40% by weight of algae, about 30% to about 60% by weight of algae, about 50% to about 80% by weight of algae, or about 60% to about 100% by weight of algae. In these embodiments, the algae can be whole algae or an extract or purified component of the algae.

In various embodiments of the methods and compositions described herein, the algae compositions can further comprise one or more of a preservative, a flavoring, an inert carrier (e.g., which can be in the form of a paste or a gel), an antimicrobial peptide, an antimicrobial (e.g., an antibiotic), a plaque-reducing agent, a calculus-reducing agent, a nutritional carrier, a nutraceutical, or other suitable additives.

In another embodiment, preservatives can be added to the algae compositions described herein. Exemplary preservatives include, but are not limited to, Thimersol, benzyl alcohol, methylparaben, propylparaben, benzoic acid, sodium benzoate, and potassium sorbate.

In an additional embodiment a flavoring may be added to the algae composition described herein. Exemplary flavorings include garlic, wood smoke, meat extracts and other meat flavorings, fish extracts and other fish flavorings (e.g., Tuna fish flavoring), fermentation residues, and any combination thereof. In embodiments where the algae composition is for treatment of the teeth of humans, flavorings can include apple, orange, cherry, vanilla, watermelon, bubble gum, apricot, grape, currant, and lemon flavorings, and any combination thereof. In still another embodiment the flavoring may be a sweetening agent, such as saccharin, dextrose, levulose, aspartame, D-tryptophan, dihydrochalcones, sodium cyclamate, sucrose, fructose, glucose, and any combination thereof.

In another illustrative aspect, an oral pharmaceutically acceptable inert carrier can be added to the algae compositions described herein. The inert carrier can be, for example, in the form of a gel, a paste, a powder, or a liquid. Exemplary inert carriers include, but are not limited to, lactose, starch (pharmaceutical grade), dextrin, dicalcium phosphate, calcium sulfate, kaolin, and mannitol.

In yet another embodiment, an antimicrobial peptide can be either expressed in the genetically modified algae that are used in the algae compositions described herein, or can be an additive to the algae compositions described herein, or a combination thereof. Suitable antimicrobial peptides include peptides that inhibit interaction or binding of microbes to components of biofilm, plaque, or calculus, peptides that interfere with the metabolism of microbes, and peptides that damage the cell walls of microbes, and the like. Exemplary methods of identifying antimicrobial peptides are known in the art, and are described in U.S. Pat. Nos. 7,465,784 and 7,393,999, incorporated herein by reference.

In still another embodiment, antimicrobial agents can be included in the algae compositions described herein. Such agents may include, but are not limited to 5-chloro-2-(2,4-dichlorophenoxy)-phenol, 8-hydroxyquinoline, copper II compounds, phthalic acid, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride, octenidine, iodine, sulfonamides, bisbiguanides, phenolics, delmopinol, octapinol, and other piperidino derivatives, and nicin preparations, any suitable antibiotics such as augmentin, amoxicillin, tetracycline, doxycycline, minocycline, metronidazole, neomycin, kanamycin, and clindamycin, and any salts of any of these compounds where applicable, and any combinations of these compounds. In another embodiment, antiviral compounds can be included, alone or in combination with any of the above-described antimicrobials. Exemplary anti-viral compounds include cytosine derivatives, purine anaglogues, pyrimidine bases, amantadines, ribavirin, zanamivir, acyclovir, and the like. In yet another embodiment, anti-fungal compounds can be included, alone or in combination with any of the above-described antimicrobials. Anti-fungals agents that are suitable for use in the algae compositions described herein include, but are not limited to, nystatin, miconazole, econazole nitrate, clotrimazole, and flucytosine.

In yet another embodiment, a plaque-reducing agent may be added such as zinc citrate, sanguinarine, chlorhexidine, baking soda, hydrogen peroxide, stannous salts, copper salts, strontium salts, or magnesium salts, and any combination thereof. Additional exemplary plaque-reducing agents include, for example, fluoride anions. In one embodiment a fluoride anion may be added such as sodium fluoride, stannous fluoride, potassium fluoride, ammonium fluoride, zinc fluoride, germanium fluoride, palladium fluoride, titanium fluoride, sodium fluorozirconate, potassium fluorozirconate, stannous fluorozirconate, stannous fluoroborate, stannous fluorosulfate, sodium fluorosulfate, potassium fluorosulfate, calcium fluorosulfate, mono fluoro phosphate, and mixtures thereof. Exemplary fluoride ion-yielding materials can be found in U.S. Pat. Nos. 3,535,421 and 3,678,154, each incorporated herein by reference.

In another illustrative aspect, a calculus-reducing agent may be added such as polyphosphates (including pyrophosphates), polyamino propane sulfonic acid, polyolefin sulfonates, polyvinyl phosphates, polyolefin phosphates, diphosphonates, phosphonoalkane carboxylic acid, polyphosphonates, polyvinyl phosphonates, polyolefin phosphonates, carboxylic acids (including malic, citric and fumaric acids), sodium hexamethaphosphate, and salts of any of these compounds, and any combination thereof.

In yet another illustrative embodiment, a nutritional carrier or supplement may be added to the algae compositions described herein. Exemplary nutritional carriers include minerals, vitamins, oral nutritional supplements, enteral nutritional supplements, and any combination thereof. Minerals that can be used include, but are not limited to, calcium, phosphorus, zinc, manganese, potassium, and any combination thereof. Suitable vitamins include, but are not limited to, vitamins C and D, thiamine, riboflavin, calcium pantothenate, niacin, folic acid, nicotinamide, pyridoxine, cyanocobalamin, para-aminobenzoic acid, bioflavonoids, and any combination thereof. Amino acids can also be added and include, but are not limited to 1-tryptophan, 1-lysine, methionine, threonine, levocarnitine, or 1-carnitine, and any combination thereof. Additional exemplary nutritional supplements include fish oils, in particular fish oils containing large amounts of omega-3 polyunsaturated fatty acids, such as eicosapentaenoic acid and docosahexaenoic acid. Enteral nutritional supplements include, but are not limited to, protein products, glucose polymers, corn oil, and safflower oil. In yet another embodiment, any of these nutritional supplements can be added in any combination.

In another illustrative embodiment, a nutraceutical can be added to the algae compositions described herein. A person skilled in the art would readily be able to determine the type(s) of anti-inflammatory agents useful for the particular animal. Suitable nutraceuticals include anti-inflammatory agents. Exemplary anti-inflammatory agents include non-steroidal anti-inflammatory agents (NSAIDs) including salicylates, propoionic acids, and fenamates, including but not limited to ibuprofen, indomethacin, diclofenac, fenoprofen, piroxicam, nabumetone, aspirin, diflunisal, meclofenamate, mefenamic acid, oxyphenbutazone, phenylbutazone, and acetaminophen. Exemplary steroidal anti-inflammatory agents include corticosteroids, such as hydrocortisone.

In another illustrative aspect, the algae compositions described herein can further comprise such additives as pharmaceutically acceptable diluents, solubilizing agents, a breath enhancing agent, an abrasive, a polish, a thickening agent, a binding agent, and an antioxidant, or combinations thereof. In various embodiments the algae compositions can include pharmaceutically acceptable diluents (e.g., liquid alcohols, glycols (e.g., polyethylene glycols), glucose solutions (e.g., 5%), esters, amides, sterile water, buffers (including phosphate or acetate buffers, isotonic saline, and Tris buffers)).

In another embodiment, the solubilizing agents can be, for example, propylene glycol, dipropylene glycol, hexylene glycol, methyl cellosolve, ethyl cellosolve, amyl acetate, ethyl acetate, benzyl benzoate, Tween 80, or Polysorbate 80.

In another embodiment a breath enhancing agent may be added to the algae compositions described herein such as oil of peppermint, oil of wintergreen, oil of spearmint, oil of clove, oil of *sassafras*, and mixtures thereof.

In various aspects, antioxidants can also be added. Exemplary antioxidants include beta-carotene, vitamin E, vitamin C, vitamin A, tocopherol, butylated hydroxytoluene, butylated hydroxyanisole, tertiary-butylhydroquinone, propyl gallate, ascorbic acid, sodium metabisulfite, uric acid, carotenoids, flavonoids, melatonin, and ethoxyquin.

In any of the above-described embodiments, the algae composition can further comprise a material to enhance adhesion of the algae to at least one tooth of an animal, and the algae can adhere to at least one tooth of an animal for a prolonged period of time, either due to the presence of an agent that enhances adhesion of the algae to the teeth, or due to the adherence characteristics of the algae. Exemplary materials that enhance adhesion of algae to at least one tooth of the animal include carbohydrates and/or carbohydrate-containing materials and proteins known in the art to enhance adherence of microorganisms to a substrate.

The following examples illustrate specific embodiments in further detail. These examples are provided for illustrative purposes only and should not be construed as limiting the presently disclosed and/or claimed inventive concept(s) or the inventive concept in any way.

EXAMPLES

Example 1: Culture and Preparation of Algae Composition

The algal cells can be cultured using a variety of techniques known in the art. Typically, algal cultures are supplemented with a carbon source (e.g., glucose or acetate), and the algal cells can be cultured to achieve a desired density. Briefly, standard sterile techniques known to those skilled in the art can be used. The algal cells can be inoculated into standard algal cell culture medium using a laminar flow hood to maintain sterile conditions and the algae can then be cultured with aeration at about 23° C. using 18 hour light/6 hour dark cycles. Progression from small cultures (e.g., 30 ml) to larger cultures (e.g., 200 ml) to large flasks (e.g., 2 liters) can be used. The algal cultures are typically stirred to maintain the cells in suspension. If the pH of the medium increases to above about 9, the culture medium can be bubbled with CO2 to reduce the pH to about 7, or an alkaline buffering compound, such as NaHCO3, can be added. When a desired algal cell density is achieved, an algal cell pellet can be collected by centrifugation, and the supernatant discarded.

Example 2: Plaque Reduction in Cats

Experiments were conducted with *C. reinhardtii* to determine if the oral delivery of the algae as a paste to the surface of the teeth of cats is an effective means to reduce plaque accumulation. Algal strains CC-741 and CC-2677 were grown for 1 week in modified Tapp media (Harris, 1989) in 20 liter carboys and harvested using a TZ28 Sorval rotor at 16,000 RPM at 4° C. Approximately 200 liters (10 carboys) were harvested for each strain. The algal paste was collected from the rotor and stored at 4° C. for approximately 1 week. The algal paste was packed into a 10 ml syringe and 1 cc of the paste was delivered to the teeth of 5 cats. Following delivery of the paste, the paste was dispersed on the surface of the teeth by manually massaging the animals' cheeks.

The results from the experiments show that plaque accumulation on the teeth of animals treated with the algal paste of strain CC-741 was less than plaque accumulation on the teeth of the control group. Four of the five animals treated with the algal paste show a reduction in the amount of plaque by 24 hours after treatment. In contrast, 3 of the 5 control animals show an increase in plaque accumulation during the same time period. One animal (Laurel) in the control group appears to deviate substantially from the response of the animals, showing a precipitous decrease in plaque accumulation. The data from the trial is provided in Tables 1, 2, 3, and 4. The results show a 24% reduction in plaque for animals treated with *C. reinhardtii* strain CC-741 (Table 1; Group A) versus controls (Table 2; Group B). The results for *C. reinhardtii* strain CC-2677 are shown in Tables 3 and 4. *C. reinhardtii* strain CC-741 is a walled algal strain and *C. reinhardtii* strain CC-2677 lacks cell walls.

TABLE 1

Plaque evaluation following treatment of feline teeth with *C. reinhardtii* strain CC-741 (Group A)

| Cat | Baseline | 24 hour |
|---|---|---|
| Grace | 6.33 | 5.17 |
| Magpie | 7.17 | 5.67 |
| Aruba | 7.00 | 5.00 |
| Lilac | 3.50 | 3.50 |
| Shirley | 5.83 | 3.33 |
| Mean | 5.97 | 4.53 |
| S.D. | 1.48 | 1.05 |
| % Change | | 24% |

TABLE 2

Plaque evaluation following treatment of feline teeth with deionized water (Group B)

| Cat | Baseline | 24 hour |
|---|---|---|
| Lily | 10.00 | 10.33 |
| Laurel | 8.67 | 4.5 |
| Kitt | 3.33 | 4.16 |
| Bora Bora | 8.33 | 8.67 |
| Audrey | 4.50 | 4.33 |
| Mean | 6.97 | 6.40 |
| S.D. | 2.88 | 2.89 |
| % Change | | 8% |

TABLE 3

Plaque evaluation following treatment of feline teeth with *C. reinhardtii* strain CC-2677 (Group A)

| Cat | Baseline | 24 hour |
|---|---|---|
| Sage | 11.8 | 8.67 |
| Robin | 7 | 7.5 |
| Maui | 6.33 | 8.67 |
| Bora Bora | 6.17 | 9.5 |
| Mean | 7.83 | 8.59 |
| S.D. | 2.67 | 0.82 |
| % Change | | 10% |

TABLE 4

Plaque evaluation following treatment of feline teeth with deionized water (Group B)

| Cat | Baseline | 24 hour |
|---|---|---|
| Figi | 2.5 | 2.67 |
| Judy | 8.5 | 9 |
| Chickadee | 7.5 | 4.8 |
| Finch | 7 | 5.67 |
| Mean | 6.38 | 5.54 |
| S.D. | 2.66 | 2.63 |
| % Change | | 13% |

Example 3: Plaque Reduction in Dogs

Thirty healthy, purpose-bred beagle dogs 1 year of age or older, with normal dental occlusion, received a full dental scaling and polishing of their teeth under general anesthesia (Day-7) (7 days before the start of the testing). On Day 0 and Day 14 each animal was placed under short acting anesthesia to evaluate the plaque indices using a modified Quigley and Hein (1962) (Turesky, 1970) plaque index after the application of a disclosing agent to the teeth followed by rinsing to remove residual excess. The teeth were visually halved horizontally into gingival and occlusive halves that were each given a score for the percentage of coronal surface covered with plaque and the thickness of plaque. The score for the tooth was obtained by adding the gingival and occlusive scores for each half (thickness multiplied by coverage). The sum of the tooth scores on one side of the jaw was termed "the total tooth score" and the whole mouth mean score is the average of the total tooth scores for each animal. On Day 0 each beagle was stratified according to high, medium and low plaque accumulation and then randomly assigned equally to either the treatment and control group. An average volume of 7 ml of *Chlamydomonas reinhardtii* concentrated algal paste, harvested live, approximately 107/ml, strain CC-741 wild-type was applied topically with a sterile 12 cc syringe daily, 2 hours after feeding, to the teeth of each beagle in the treatment group. The control beagles received no treatment. All dogs in the study were fed a standard dry diet. Daily application of algae paste resulted in a 6.8% (SD 2.1) reduction in mean plaque scores compared with control beagles that received no treatment. Table 5 demonstrates that when the plaque scores are rank ordered, the paired comparisons showed the same plaque scores for the highest 6 beagles in the treatment and control groups, while the remaining 9 beagles in the treatment group all had lower scores than their comparative control group ranked pair. Further, the treatment group had the lowest overall plaque scores of 5.5 (2 beagles) compared to the lowest score of 6.6 in the control group. These data indicate that *Chlamydomonas* algal paste contacting the teeth of beagles reduces plaque formation.

TABLE 5

Plaque scores in Beagles (control and treatment groups)

| Dog | Control | Treatment |
|---|---|---|
| 1 | 12.1 | 12.1 |
| 2 | 10.9 | 10.9 |
| 3 | 10.8 | 10.8 |
| 4 | 9.5 | 9.5 |
| 5 | 9.2 | 9.2 |
| 6 | 9.0 | 9.1 |
| 7 | 8.9 | 8.4 |
| 8 | 8.8 | 8.3 |
| 9 | 8.7 | 7.1 |
| 10 | 8.6 | 6.9 |
| 11 | 7.4 | 6.8 |
| 12 | 7.3 | 6.5 |
| 13 | 7.2 | 6.2 |
| 14 | 6.7 | 5.5 |
| 15 | 6.6 | 5.5 |
| Average | 8.8 | 8.2 |
| Stand. Dev. | 1.6 | 2.06 |

Example 4: Plaque Reduction Assay a. General Test Design. To evaluate the various algae preparations a series of at least 3 screening tests are performed to identify preparations for the prevention of dental plaque formation in animals. The screening tests are designed as 7-day longitudinal studies with parallel groups of 5-10 animals. This is followed by a complete crossover test to demonstrate the anti-plaque potential of the preparations selected from the screening tests.

b. Test Procedures. Each screening test is designed as a one-week (7-day) clean tooth longitudinal test design. The test agents are applied to the animals' teeth 3 times daily M-F and 2× daily on the weekends with applications separated by at least 2 hours. Experimental procedures are conducted using GLP guidelines. The animals are fed a nutritionally complete commercially-available dry dog food (Purina Dog Chow) at approximately 10:00 a.m. daily.

Prior to the initiation of each study, the animals are given a complete dental prophylaxis to remove all exogenous deposits (plaque, calculus, stain, debris) from the surfaces of their teeth. On the day each screening study will begin, the animals are given Atropine (0.04 mg/Kg) by s.c. injection 20 minutes prior to the anesthesia. A certified laboratory animal technician anesthetizes the dogs with Butorphanol (0.15 mg/Kg) and Medetomidine (0.025 mg/Kg) I.M. followed by Ketamine HCL (5.0 mg/Kg) I.M. The animals are then given a thorough prophylaxis. Following the dental prophylaxis, the animals' teeth are imaged using the QLF System. The animals are then given Atipamezole (0.05 mg/Kg) I.M. as an anesthesia reversal. The animals are evenly stratified by block design into the desired number of groups of at least 5 animals per group. The animals are balanced on the basis of plaque data obtained from the most current plaque-forming rate study. Considering the number of preparations to be evaluated, it is expected that each screening test will involve 5 groups with 5 or 6 animals per group. The test materials are topically applied individually to the animals' teeth as an aqueous slurry using a syringe. Three (3) treatments are given on week-days (Monday-Friday) and two (2) treatments are administered on Saturday and Sunday; only one treatment is given on the day the animals are prophied. The treatments are performed at approximately the same time every day with 2-hour intervals between treatment applications. Each treatment group has a coded beaker, which is designated for that treatment only. Each test group has a color-coded tag attached to the animal's cage to correspond with the coded test group. The test solutions are applied to all of the maxillary and mandibular teeth in their assigned treatment group. A 5 cc syringe is used to apply the solution. Specifically, 2.5 cc of each test solution (within the appropriate group) is evenly dispersed to each hemi jaw over the teeth to be evaluated and allowed to pool in the mandibular region. No attempt is made to prevent the animals from swallowing the solutions. Care is taken to prevent the disturbance of naturally occurring plaque. On the designated examination day, 7 days after initiation of the treatment regimen, the animals are examined by block in a random sequence to avoid systematic bias. The animals are anesthetized as previously stated, taken to the examination area by a certified laboratory animal technician.

The animals then have their teeth imaged using Quantitative Laser/Light Fluorescence (QLF). The animals are then examined for oral malodor, and disclosed plaque. Examiner observations are recorded on prepared exam forms by the recorder who is not directly involved in the examinations. Baseline Quantitative Laser Florescence exams are done immediately following the dental prophylaxis and after 7-days while the animals are still under anesthesia. The animals are examined in a random sequence to avoid systematic bias. The examinations are performed independently by an experienced QLF examiner. Specifically a hand piece utilizing a high intensity halogen light source, a video camera, and a mirror for focusing, are placed on the buccal side of the each of the following teeth:

Maxilla: $I_3$, C, $P_2$, $P_3$, $P_4$, $M_1$
Mandible: C, $P_2$, $P_3$, $P_4$, $M_1$ The QLF hand piece is coupled to a computer to permit visual viewing and recording of the images. The distance and angle of the QLF hand piece remains essentially constant for each tooth imaged using the video repositioning (VidRep) program at 90-95%. A Halimeter is used to measure Volatile Sulfur Compounds (VSC). The sampling tube is placed parallel to the buccal Maxillary $P_4$. Cheek mucosa is kept away from the end of the sampling tube and the animal's mouth closed. The highest reading after a 10-second period is recorded. Both right and left sides are sampled. The score for the animal is the mean of these two readings.

For the visual clinical dental plaque examinations, the plaque is disclosed by applying the undiluted disclosing solution (Red Cote; John O. Butler Company; 1.5% D&C Red No. 28) to the buccal surface of each tooth with a syringe and immediately rinsing with water. The gingival and occlusal half for each tooth is scored. The teeth that are examined are:

Maxilla: $I_3$, C, $P_2$, $P_3$, $P_4$, $M_1$
Mandible: C, $P_2$, $P_3$, $P_4$, $M_1$ The amount of the buccal surface covered with dental plaque is visually graded using the following scale: 0=no observable plaque; 1=scattered plaque covering less than 24% of the tooth surface; 2=plaque covering between 25 and 49% of the tooth surface; 3=plaque covering between 50 and 74% of the tooth surface; 4=plaque covering more than 75% of the tooth surface. The thickness of the plaque is estimated using the following scale: 1=Light; 2=Moderate; and 3=Heavy. The clinical plaque score is a function of both the coverage and the thickness. The coverage score is multiplied by the intensity factor to give a gingival and occlusal score for each tooth. The gingival and occlusal values for each tooth are added together to obtain a tooth sum. The score for each animal is the mean sum for all teeth scored. These same procedures are used for the complete crossover study. For the first leg of the study the animals is randomized to either the test or placebo treatment and examined after the 7-day test period. The animals then have a one-week "washout" period and are then provided another dental prophylaxis followed by the initiation of the alternative treatment regimen. In this manner all animals receive both the test and placebo treatments with the test concluded after the second leg or test period.

Example 5: Plaque Reduction Assay

*Chlamydomonas reinhardtii* concentrate live or freeze dried, or in combination with synergistic agents, and various application methodologies are used. This phase runs for a total of 7 days. Dogs chosen for use on the study have their teeth scaled and polished upon initiation of the test (Day-7). Each animal has plaque indices scored on Day 0 before dental cleaning. The scores indicate the rate of plaque buildup for each animal when being fed only a standard diet. This Pre-Test information is used to designate the animals in one of three groups so as to stratify the group as a whole to reduce variability for the Testing Period.

Day 0 through Day 14 is the testing period in which the test article, along with a standard diet, is offered on a daily basis to the dogs within the test group for evaluation of plaque buildup as compared to evaluation of the control group, which is offered only a standard diet.

A minimum of 20 animals (e.g., Purpose-bred Beagle dogs) 1 year of age and older are used. Groupings are determined by evaluating the animals' individual scores obtained from the pre-testing period. Based on individual scores, 10 dogs are in the test group, and 10 dogs are in the control group. Each dog has a unique ear tattoo and cage card for identification.

Healthy adult dogs meeting the above description are eligible for the study. Before the start of the study, dogs undergo an oral cavity examination for normal occlusion and presence of all test teeth. Dogs are pair-housed as intended for this study prior to study initiation. Individual body weights are measured and recorded upon initiation of the study, weekly throughout the study, and upon completion of the study. Standard colony diet is meal-fed, checked daily, and supplied in appropriate amounts according to body weight prior to study initiation.

Dogs in the test group receive the standard diet for one hour, and the test article is applied two hours after the standard diet is removed from the dog's enclosure. The volume of test article required is 10 milliliters per treatment dog per day to be topically applied with a sterile 12 cc syringe. The control group does not receive anything in addition to the standard diet. Food consumption is recorded daily throughout the study.

A veterinarian gives a complete physical examination to all dogs prior to Day-7. Each dog is evaluated as to general health, body, and hair coat condition, and comments are recorded. Two milliliters of blood are taken from each dog to test for BUN, PCV, and TP at the physical examination, if this data has not been updated within the last 6 months.

Each animal has its teeth scaled and polished under general anesthesia on Day-7. Each animal has a plaque index scored at Day 0 using sedation or short-acting anesthesia. The extent of plaque is recorded after staining with a disclosing agent and rinsing the tooth surface. The dogs are offered the standard diet only during this time period.

Each animal has its teeth scaled and polished under general anesthesia on Day 0. On Day 14, each animal has plaque evaluated using sedation or short-acting anesthesia if needed. The examination of teeth includes the buccal surfaces and both sides of the mouth. Review is limited to these nine teeth: upper jaw—incisor 3 ($I_3$), canine (C), premolar 3 ($P_3$), premolar 4 ($P_4$), molar 1 ($M_1$); lower jaw—canine (C), premolar 3 ($P_3$), premolar 4 ($P_4$), molar 1 ($M_1$).

Oral malodor is evaluated on Day 0 and Day 14 by using a Halimeter. Readings are obtained by putting the straw end of the Halimeter into the dog's mouth, between the cheek and jaw. A pocket is made, and the lips are closed around the straw to assure accurate readings. One reading is taken on each side of the mouth and recorded in ppb.

Plaque is evaluated using a modification of the Quigley and Hein (1962) (Turesky, 1970) plaque index. The extent of plaque and plaque thickness is determined by placing a disclosing agent on the teeth and rinsing the excess off with water. The teeth are visually halved horizontally into gingival and occlusal halves. Each half is given a score for the percentage of coronal surface covered with plaque and thickness of plaque. The score for each half is calculated by multiplying the coverage and thickness scores. Gingival and occlusal scores are then added together for a tooth score. The sum of the tooth scores on one side of the jaw is termed the total tooth score, and the whole mouth mean is calculated by averaging the total tooth scores for each animal.

TABLE 6

Plaque Scoring Method
PLAQUE SCORING METHOD

| Score | % of Plaque Coverage | |
|---|---|---|
| 0 | No plaque detected | |
| 1 | 1-24 | |
| 2 | 25-49 | |
| 3 | 50-74 | |
| 4 | 75-100 | |

| Score | Plaque Thickness | Disclosing Agent Color |
|---|---|---|
| 1 | Light | Pink to Light Red |
| 2 | Medium | Red |
| 3 | Heavy | Dark Red |

Qualified personnel perform clinical observations twice daily in accordance with institutions animal care observation standards. All animals are evaluated twice daily with reference to protocol for (Recognizing Pain, Stress, and/or Distress). Clinical laboratory diagnostic procedures are performed as needed. Veterinary care is given as appropriate to each individual animal in accordance with the Program of Veterinary Care.

Test Article may vary by each individual trial. Test article consistency is a sticky paste/gel that will be drawn from a container into sterile syringes. The test article is then administered onto the teeth via syringe. The test article is stored in refrigeration for the duration of the study.

With the exception of drugs used to anesthetize the animals for dental scoring and cleaning, vaccinations, drugs, and locally applied or lickable antiseptics should not be used for the length of the study. If an individual animal requires treatment as determined by the veterinarian, the Sponsor is notified, and the necessity of removing the animal from the study is determined. The study is stopped if the average weight change of the dogs is greater than −10%. If any dog loses more than 15% of its base (initial) weight, that dog is evaluated by the veterinarian and removed from the study if the veterinarian deems it necessary to do so. The study may be stopped at any time at the veterinarian's discretion if the animals' health is at risk. A veterinarian performs a necropsy on any animal found dead or euthanized to determine the cause of death or illness.

Variables measured include the effect of *Chlamydomonas reinhardtii* on the formation of dental plaque, the effect of *Chlamydomonas reinhardtii* on the formation of dental malodor, and the effect of *Chlamydomonas reinhardtii* on the formation of dental calculus. Other variables measured include food consumption, body weights, and adverse reactions through daily observations. Statistical analysis includes individual t-tests, mean scores, and standard error functions.

Example 6: Molars Treated with Algal Paste

A total of 6 extracted human molars (a tooth in each group) were used for this study. These specimens were removed of soft tissue. A window was made on the surface of sound enamel specimen by nail varnish. These specimens were immersed into demineralizing solution (White, 1987) at 37° C. for 2 hours to produce the early artificial white-spot lesions. The whole surface of each molar was covered with an algal strain. After 5 minutes, each molar was shaken in a water bottle for 30 seconds and any surplus alga was rinsed off. The images of these specimens were acquired with a standard white-light dissecting microscope. Digital images of the molar prior to treatment and after rinsing were recorded. After the 30 second rinse, strains CC-1284, CC-741, and Phyvac WSSV-VP28 were not evident on the enamel surface lesion, suggesting a low level of enamel adherence. Strains CC-1284 and CC-2677 adhered to parts of the surface whereas CC-1952 covered the whole surface of the molar.

Figure 2:
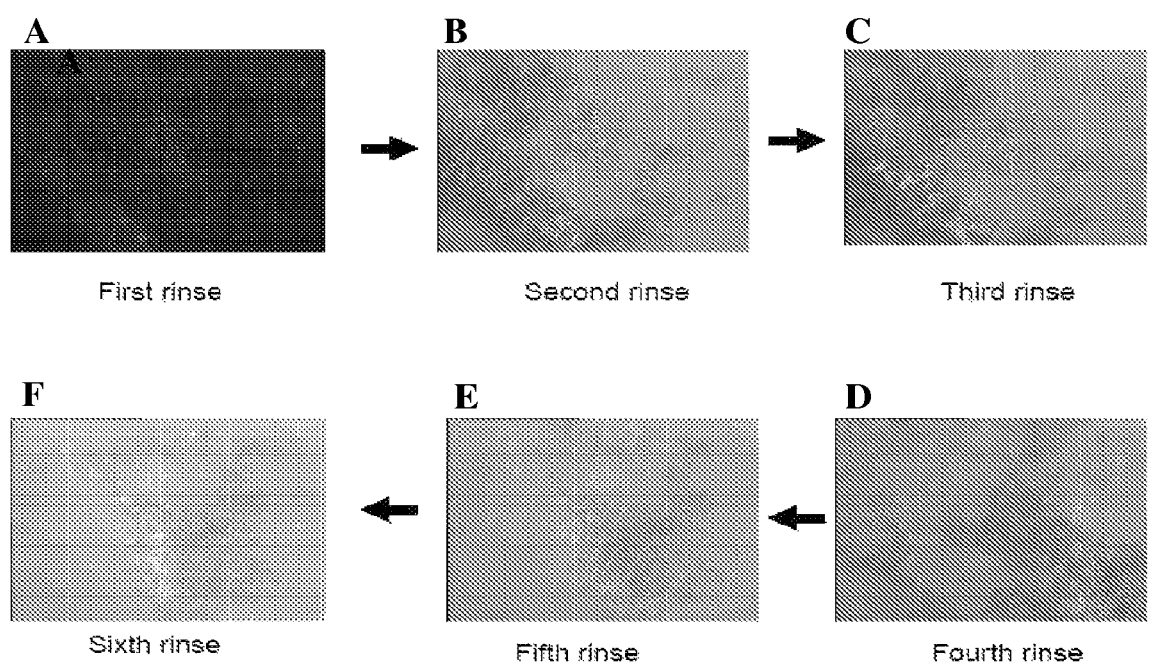
FIG. 2 shows cells of CC-1952 remaining on a molar following coating the molar with an algal paste and successive rinses with deionized water. Panels A-F represent the first through sixth rinses, respectively.

The experiment was repeated again, with the rinsing treatment repeated 6 times. CC-2677 was removed from the surface after the second rinse. CC-1284 and CC-1952 could not be removed after the sixth rinse, although adherence of strain CC-1952 to the tooth surface was greater than for CC-1284 (FIGS. 1 and 2).

Figure 3:
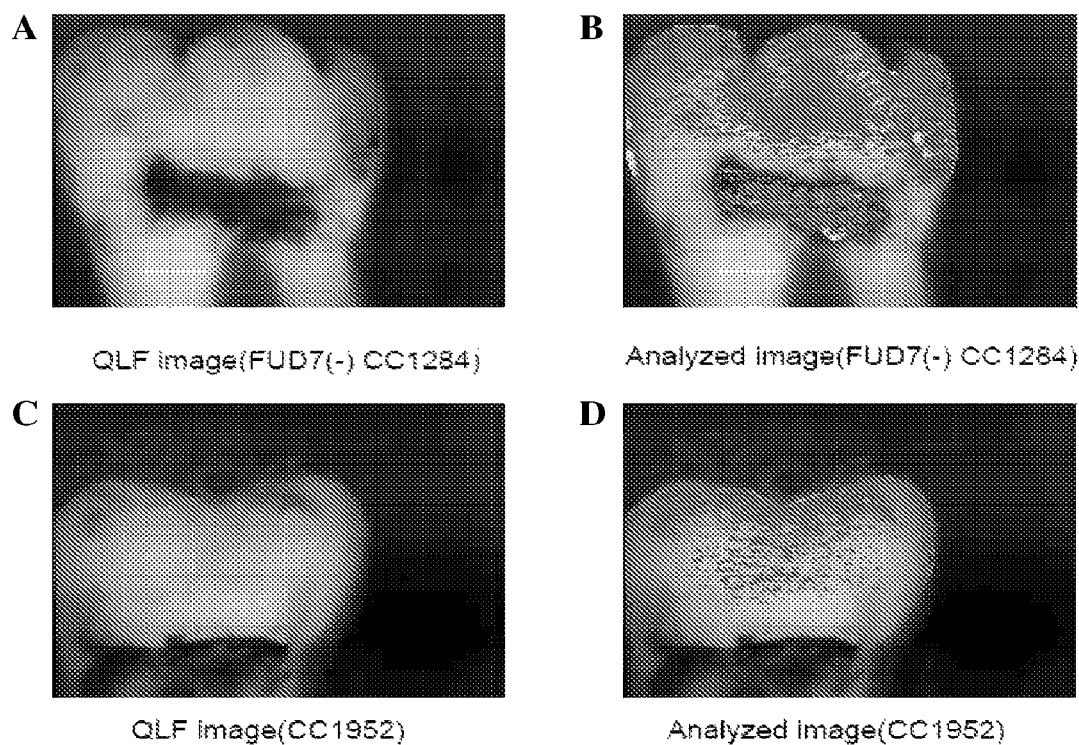
FIG. 3 shows the quantitative light-induced fluorescence imaging of molars coated with an algal paste from CC-1284 (Panels A and B) and CC-1952 (Panels C and D) before (Panels A and C) and after (Panels B and D) rinsing six times with deionized water.

The rinsing experiment was repeated a third time with CC-1284 and CC-1952. After the sixth rinse, digital images of specimens were made using the Quantitative Light-induced Fluorescence system (Inspektor-Pro 2.0.0.32, Inspektor Research System B.V., Netherlands). These images were analyzed with the measurement for red fluorescence using Inspektor-Pro 2.0.0.32. QLF images and its analyzed images are shown in FIG. 3. From these images it was calculated that after the sixth rinse, 16.60 $mm^2$ and 45.60 $mm^2$ of the molar surface was covered with cells of CC-1284 and CC-1952, respectively.

Example 7: Toothpaste

An exemplary animal toothpaste formulation for use in the compositions and methods described herein is below. Sample ingredients for the toothpaste are as follows (expressed as percent by weight): dental grade silica abrasive at about 10-12% (gives polishing abrasion and thickens toothpaste); dicalcium phosphate dihydrate at about 2-4% (dentifrice grade toothpaste polish and abrasive); pumice (a toothpaste polish and 1-2% abrasive); toothpaste thickening and binding agents, such as sorbitol at about 10-40%, polyethylene glycol at about 4%, carboxymethylcellulose at about 1%, glycerin at about 15%, flavor at about 1-3%, the algae composition at about 5% (or another effective amount depending on the intended application), and water sufficient for processing. Toothpaste formulations for humans may also include surfactants (cleaning and foaming agents). Toothpaste formulations for animals other than humans typically do not include surfactants. The formulation may also include about 2% sodium fluoride in a suitable form.

Example 8: Chew Treat

The algae composition as described herein may be added to raw hide as a chew treat to improve animal dental health. The raw hide is made from cattle hides, horse hides, sheep skins, goat skins, buffalo hides or pig skins, for example. The raw hide may be cut into sections or strips. Alternatively, the raw hide sections may be ground into smaller pieces of about ⅛ inches to about ½ inches in diameter, for example, and dried. The algae composition may be sprayed onto the dried raw hide pieces. In this embodiment, the pieces can be placed in a rotating mixing drum and the algae composition sprayed onto the tumbling pieces or chews. Following the coating (spraying) step, the product is placed on screens in racks and air dried. The resulting chew treats containing the algae composition may be molded into the shape of a animal chew treat.

Another exemplary approach is to mix the algae composition and dried raw hide with meat meal, bone meal, a binder such as malotdextrin, and/or gelatin. Water is added in a quantity sufficient for processing. The formula is heated, mixed, and placed into molds. After molding into suitable shapes, the product is dried in an oven.

Example 9: Toothpowder

An exemplary powder formulation for use in the compositions and methods described herein is provided. According to the following formulation (components expressed as percent by weight), the ingredients are mixed well to make a fine powder, including calcium carbonate at about 75.0%, glycerin at about 10.0%, flavor at about 1.0%, propylparaben at about 0.005%, sodium laurylsulfate at about 1.3% (typically used only for formulations for humans), saccharin sodium at about 0.1%, the algae composition at about 5% (or another effective amount depending on the intended application), and water q.s. total 100%.

An additional exemplary toothpowder formulation with fluoride is made by mixing together the following ingredients (components expressed as percent by weight), in the indicated proportions: microcrystalline aluminum hydroxide at about 86%, aluminum hydroxide (325 mesh) at about 5.00%, flavoring matter at about 0.60%, saccharin (soluble) at about 0.25%, sodium fluoride at about 0.10%, the algae composition at about 10%, and water.

What is claimed is:

1. A composition comprising:
    a manufactured, oral plaque-reducing product selected from the group consisting of an additive to drinking water of an animal, a non-digestible chew product formulation, a toothpaste formulation, a toothpowder formulation, and a toothgel formulation, wherein the manufactured, oral plaque-reducing product comprises:
    a therapeutic amount of whole green microalgae, wherein the microalgae are *Chlamydomonas* microalgae, wherein the microalgae are grown under sterile conditions, and wherein the microalgae are not genetically engineered; and
    wherein the composition is formulated for topical application to the surface of at least one tooth of an animal, and wherein the therapeutic amount reduces plaque on the surface of the at least one tooth of the animal.

2. The composition of claim 1, wherein the algae are freeze-dried and are capable of being reconstituted.

3. The composition of claim 1, wherein the algae are in a form selected from the group consisting of a paste, a gel, a nugget, a pellet, a powder, and a liquid.

4. The composition of claim 1, wherein the algae composition further comprises an antimicrobial.

5. The composition of claim 1, wherein the algae composition further comprises a plaque-reducing agent.

6. The composition of claim 1, wherein the algae are *Chlamydomonas reinhardtii*.

7. The composition of claim 1, wherein the algae are selected from the group consisting of live algae, dead algae, and combinations thereof.

8. The composition of claim 1, wherein the animal is a domestic animal.

9. The composition of claim 1, wherein the animal is a dog.

10. A kit, comprising:
    the composition of claim 1.

11. The kit of claim 10, further comprising an applicator for rubbing the composition on the at least one tooth of the animal.

12. A method for reducing plaque on at least one tooth of an animal, the method comprising the steps of:
    causing the at least one tooth of the animal to be contacted with the composition of claim 1, wherein the composition reduces the plaque on the at least one tooth of the animal.

13. The composition of claim 1, wherein the manufactured, oral plaque-reducing product is an additive to drinking water of an animal.

14. The composition of claim 1, wherein the manufactured, oral plaque-reducing product is a non-digestible chew product formulation.

15. The composition of claim 1, wherein the manufactured, oral plaque-reducing product is a toothpaste formulation.

16. The composition of claim 1, wherein the manufactured, oral plaque-reducing product is a toothpowder formulation.

17. The composition of claim 1, wherein the manufactured, oral plaque-reducing product is a toothgel formulation.

* * * * *

UNITED STATES PATENT AND TRADEMARK OFFICE
CERTIFICATE OF CORRECTION

| | | |
|---|---|---|
| PATENT NO. | : 11,490,639 B2 | Page 1 of 1 |
| APPLICATION NO. | : 15/269176 | |
| DATED | : November 8, 2022 | |
| INVENTOR(S) | : Richard E. Wagner | |

It is certified that error appears in the above-identified patent and that said Letters Patent is hereby corrected as shown below:

In the Specification
Column 9, Line 66: After "precipitation," delete "DEAF-dextran" and replace with
-- DEAE-dextran --

Signed and Sealed this
Third Day of January, 2023

Katherine Kelly Vidal
*Director of the United States Patent and Trademark Office*